US005248500A

United States Patent [19]

Ayanaba

[11] Patent Number: 5,248,500

[45] Date of Patent: Sep. 28, 1993

[54] **SLOW-RELEASE BIODEGRADABLE GRANULES OF *PASTEURIA PENETRANS***

[75] Inventor: Abateni Ayanaba, Oakland, Calif.

[73] Assignee: Del Monte Corporation, San Francisco, Calif.

[21] Appl. No.: 631,688

[22] Filed: Dec. 21, 1990

[51] Int. Cl.$^5$ .............................................. C12N 1/21

[52] U.S. Cl. .............................. 424/93 K; 424/93 D; 424/417; 424/418

[58] Field of Search .................. 424/93 K, 93 D, 417, 424/418, 195.1

[56] References Cited

U.S. PATENT DOCUMENTS

| | | | |
|---|---|---|---|
| 4,668,512 | 5/1987 | Lewis et al. | 424/93 |
| 5,089,263 | 2/1992 | Spiegel et al. | 435/253.3 |
| 5,094,954 | 3/1992 | Previc et al. | 435/242 |

FOREIGN PATENT DOCUMENTS

WO8901034 2/1989 PCT Int'l Appl. .

OTHER PUBLICATIONS

Silbiger et al. CA 108:185306, 1987.
Thomason, I. J., et al., 1960, Plant Disease Reporter 44:354-358.
Lewis, J. A., et al. (1987) Plant Pathology 36:438-446.
Sayre, R. M. (1980) Plant Disease 64:527-532.
Mankau, R., et al., 1977, J. Nematol. 9, 40-45.
Bashan, Y., 1986, Appl. Env. Microbiol. 51, 1089-1098.
Stirling, G. R., et al., 1980, Nematologica 26, 308-312.
Connick, W. J., Jr., 1988, In: Pesticide Formulations: Innovations and Development, Ed: B. Cross and H. B. Scher, pp. 241-250.
Fravel, D. R., et al., 1985, Phytopathology 75, 774-777.

*Primary Examiner*—Douglas W. Robinson
*Assistant Examiner*—Jean C. Witz
*Attorney, Agent, or Firm*—Flehr, Hohbach, Test, Albritton & Herbert

[57] ABSTRACT

Biocontrol particles for treating plants infested with nematodes. The biocontrol particles are granules consisting of spores of bacterial nematicides which are contained in a biodegradable gel matrix formulated for controlled spore release. The bacterial spores are obtained by growing bacteria in nematode hosts which are in turn infesting plant roots. The roots are comminuted and used to prepare either dried or fresh inocula, which are then encapsulated into gel beads. Included in the method is a heat-treatment which kills the nematodes while maintaining the viability of the bacterial spores. To kill or inhibit the reproduction of nematodes, the biocontrol granules are deposited near plants or sowed with seeds, after which spores are released gradually through the biodegradation of the gel matrix of the granules.

9 Claims, No Drawings

SLOW-RELEASE BIODEGRADABLE GRANULES OF *PASTEURIA PENETRANS*

BACKGROUND OF THE INVENTION

The phylum Nematoda encompasses a group of unsegmented worms, of which approximately 2000 are known plant parasites. Nematodes parasitize the roots of a diverse collection of important food plants, including tomato, bean, sugar cane, peach, banana, pineapple and citrus.

In a well-balanced ecosystem, the multiplication of nematodes is checked by a variety of natural phenomena, including organisms which parasitize the nematode. In a cultivated field, however, nematodes may proliferate excessively, to the point of harming or destroying the crop.

The identification of bacterial parasites which infest nematodes suggested that these bacteria could be exploited for the control of nematodes in agriculture. One example of such a microbial nematicide is *Pasteuria penetrans* (also known as *Bacillus penetrans*), which is a bacterial endoparasite of several economically important namatodes, including *Pratylenchus scribneri* and four species of Meloidogyne. (Mankau, R. et al, 1977 *J. Nematol.* 9, 40-45.)

*P.penetrans* controls the multiplication of nematodes principally by destroying their reproduction. Spores of *P. penetrans* attach to the cuticle, or outer coat, of the developing female nematode, penetrate into its body cavity, and replicate therein. Infestation with multiplying *P. penetrans* prevents any significant nematode reproduction because physiological processes of the infected female nematode are taken over to promote *P. penetrans* reproduction. In a secondary form of biocontrol, spores infect a nematode, weakening it, and thereby reducing its infective capacity or rendering it susceptible to attack by other parasites and to pathogens (Davies, K. G. et al, 1988 *Ann. Appl. Biol.* 112, 491-501).

In order to exploit the bacterium *P. penetrans* as a biocontrol agent, a source for the bacteria is needed. Many types of bacteria can be grown under in vitro culture conditions (see for example, Bashan, Y. 1986 *Appl. Env. Microbiol.* 51, 1089-1098). However, since *P. penetrans* is an obligate parasite of nematodes, in vitro culture conditions have not been found to support the bacterial life cycle, and bacterial spores must be grown in and obtained from nematodes. Air-dried preparations of *P. penetrans* spores have been obtained from nematode-infested plant roots and tested for potential commercial use (Stirling, G. R., et al. 1980 *Nematologica* 26, 308-312; Stirling, G. R. 1984 *Phytopathology* 74, 55-60; Dube, B., et al, 1987 *J. Nematol.* 19, 222-227). Such preparations are limited in usefulness because the air-dried preparations are likely to contain viable nematodes or their eggs, which would further infest any field to which the spores were applied. Moreover, the powdery root preparations are not compatible with agricultural machinery. Clearly, alternative means for the agricultural application of microbial nematicides are needed.

Microencapsulation has been used for the packaging of living organisms within bead-like gels (Connick, W. J., Jr. 1988, In: *Pesticide Formulations: Innovations and Development,* Ed: B. Cross and H. B. Scher, pp. 241-250). For instance, sodium alginate solutions, upon exposure to metal cations such as calcium, form bead-like gels in which organisms may be entrapped. Upon exposure to the proper environment, the entrapped material is released at a rate controlled by the original formulation of the gel. Alginate beads are biodegradable and non-polluting.

Alginate gel has been used for the microencapsulation of beneficial bacteria and fungi grown in culture systems which exclude undesired plant pathogens. Biocontrol fungi were grown on agar plates or in fermentation vessels, and the wet fungal biomass was incorporated into alginate granules (Walker, H. L., et al, 1983, *Weed Sci.* 31, 333-338; Lewis, J. A., 1987, *Phytopathology* 75, 774-777; Fravel, D. R., et al, 1985 *Phytopathology* 75, 774-777). Biocontrol granules containing viable fungi were applied to soil in order to kill weeds or plant pathogenic microorganisma (Walker, H. L., Supra; Lewis, J. A., Supra). Beneficial rhizosphere bacteria were grown in culture systems free of plant pathogens and incorporated into alginate biocontrol granules, which were sowed concomitantly with seeds in order to promote plant growth (Bashan, Y. 1986, Supra.

SUMMARY OF THE INVENTION AND OBJECTS

This invention relates to biocontrol particles containing viable spores of *Pasteuria penetrans* bacteria which are essentially free of viable nematodes, and which are formulated and dried for controlled release of spores in an agricultural environment. The biocontrol granules of this invention are produced from inoculum made from bacteria grown in nematode hosts on plant roots. The inoculum is subjected to heat-treatment designed to kill nematodes while maintaining the viability of bacterial spores. The heat-treatment is applied preferably before the inoculum is encapsulated in gel material to form beads. Alternatively, the heat-treatment is applied after encapsulation of inoculum into beads and during the subsequent drying of the beads to form granules.

It is an object of the present invention to provide particles which kill or control the proliferation of nematodes by supplying bacterial spores which parasitize the nematodes.

It is a further object of the invention to provide biocontrol particles which degrade at a predetermined rate to supply controlled release of the bacterial spores.

A further object of the present invention is to provide a method for forming such biocontrol particles from nematode infested roots wherein nematodes will be killed while the viability of the bacterial spores will be maintained.

It is a further object of the present invention to provide a method to kill or prevent the reproduction of nematodes by depositing granules near the infected plants or by sowing the granules concomitantly with seeds.

DETAILED DESCRIPTION OF THE PREFERRED EMBODIMENTS

Definitions

The term "biocontrol" is defined as the killing or the inhibition of proliferation of a nematode.

The term "spore" is defined as the resting body of the bacterium that is resistant to unfavorable environmental conditions and produces new individual bacteria when the environment is favorable. In the case of spores of *P. penetrans,* for instance, the favorable environment is the body cavity of a nematode.

The term "attachment" refers to the active step whereby a spore infects a nematode.

The term "inoculum" refers to material that is used to implant microorganisms into biocontrol beads or granules.

The term "biodegradable" refers to a substance which can be broken down by microorganisms, or which spontaneously breaks down over a relatively short time (within 2–15 months) when exposed to environmental conditions commonly found in nature.

The term "bead" refers to a particle, typically spheroidal, composed of a gel-like substance which contains an entrapped biocontrol agent.

The term "granule" refers to a bead which has been dried to a moisture content below about 15%.

The term "ambient room temperature" refers to a temperature between about 15° to 40° C. surrounding beads or granules in a space without externally supplied heat.

According to this invention, biocontrol granules are produced by the steps of: 1) growing biocontrol bacteria in nematodes infesting plant roots; 2) preparing inoculum from roots of the infested plants; 3) entrapping the inoculum within biodegradable gel to form biocontrol beads; and 4) drying the beads to form biocontrol granules. During either step 2 or step 4 of the method of the invention there is included a heat-treatment designed to kill nematodes while maintaining the viability of the biocontrol bacteria The following is a description of a first alternative process.

First, bacteria intended for biocontrol of nematodes are produced by allowing their proliferation within host nematodes, which are in turn infesting plant roots. In a preferred embodiment of the invention, the tomato plant (*Lycopersicon esculentum* cv. Ace) is infected with second stage juveniles of the nematode *Meloidogyne incognita,* which are encumbered with spores of the bacterial nematode parasite *Pasteuria penetrans.* The plants are maintained in the greenhouse for 10–12 weeks, during which time the bacterial spores proliferate.

Then, the roots bearing nematodes and spores are heat-treated under conditions which are lethal to a substantial portion of the root-knot nematodes of the Meloidogyne species. (Thomason, I. J., et al, 1960 *Plant Disease Reporter,* 44, 354–358. The term "lethal for a substantial portion" means that most, or substantially all, or most preferably all of the nematodes and nematode eggs are rendered non-viable. Conditions which are lethal for nematodes, which also maintain the viability of *P. penetrans* spores, are exposure of roots to temperatures between about 48° C. to 52° C. for a duration, say, of about 12 to 48 hours, preferably 24 to 36 hours, depending upon the temperature. The heat-dried roots are then comminuted in a blender and passed through a mesh screen to produce fine particles for encapsulation. The size of the mesh screen may be from 45 microns to 425 microns or more (325 to 35 mesh), and preferably 106 microns to 425 microns (150 mesh to 35 mesh), and most preferably 425 microns (35 mesh). The comminuted roots are screened in order to obtain particles fine enough to produce a slurry in the ensuing mixing step described below.

Then the beads are formed as follows. The root preparation is mixed with distilled water and a biodegradable gel material to form a slurry. The biodegradable gel material may be a polymeric substance such as a protein (gelatin, casein), cellulose, or vegetable gum (agar, carrageenin, sodium alginate).

Sodium alginate is a preferred gel material. It is a water soluble polysaccharide gum which is extracted from the brown seaweeds (Connick, 1988, Supra). Sodium alginate is commercially available in either low or medium viscosity, either of which may be used in practicing this invention. Mixtures are prepared to yield final concentrations of about 1 to 5% root inoculum, more preferably about 1 to 3% root inoculum, most preferably 1% root inoculum. The final concentration of sodium alginate in the mixture is about 0.5 to 6%, more preferrably about 1 to 2%, most preferrably 1%.

Concomitant with mixing of the root/gel mixture, bulking agents may be added, if desired, to improve handling of the final granule preparation. Bulking agents may be selected from a group of substances such as clays (e.g. kaolin), silicagels, hydrophobic polymers, and hydrophilic polymers (Fravel, D. R. 1985, Supra). Suitably, the root/gel mixture includes a final concentration of about 5 to 20% bulking agent (e.g. kaolin), preferably about 8 to 12%.

The alginate/root slurry is added dropwise to a cross-linking agent, suitably a divalent cation such as calcium, in a calcium chloride solution. Preferably, the calcium chloride solution is about 0.05 to 0.5M, more preferably about 0.1 to 0.2M, most preferrably 0.1M. Beads form instantaneously upon contact of the drops of alginate/root slurry with the calcium chloride solution.

Thereafter, the beads are dried, preferably to a moisture content of less than about 15% by one of two means: A) air-drying at ambient temperatures between about 15° to 40° C., or B) heat-drying at temperatures between about 48° to 52° C. Dried beads are more suitable for commercial use than wet beads due to greater shelf life, ease of handling, and compatibility with agricultural machinery. The beads resulting from the first alternative process may be air-dried rather than heat-dried for savings in time and energy. Although two heat treatments do not compromise the viability of the bacterial spores, only one heat treatment is necessary for the killing of nematodes.

In a second alternative process, the roots bearing nematodes and spores are not heat-treated prior to bead formation. Roots may either be prepared fresh, comminuted in a blender, and passed through a mesh screen of 425 or 1000 microns (35 or 16 mesh), or the roots may be air-dried, comminuted, then passed through a mesh screen as described in the first alternative process above. Either of these two root preparations yields root inoculum bearing viable nematode forms as well as spores. Air-drying of the roots does not kill the nematodes because only temperatures in excess of 45° C. are lethal to certain stages of the nematode life-cycle (Thomason, I. J., et al, 1960, Supra).

The wet or air-dried root particles are then encapsulated within biodegradable gel material to form beads as described above.

In this process, the beads are subjected to the heat-treatment applied to roots in the first alternative process for the dual effect of killing nematodes while drying the beads to form granules.

The dried particles resulting from the first or second alternative processes are the biocontrol particles, or granules, as defined in the present invention. These granules contain viable bacterial spores, as evidenced by bioassays, in vitro and in planta, described in the examples below.

Other bioactive agents may be co-encapsulated along with spores. These co-encapsulated agents may include plant nutrients such as phosphates, substances that could enhance spore attachment to nematodes, other spore-forming biocontrol agents or plant hormones.

It is preferred to deposit biocontrol granules near plants infected with nematodes in order to kill the nematodes or to inhibit their proliferation. Similarly, the biocontrol granules may be mixed with seed and deposited at the time of sowing, since the present invention enables the production of biocontrol granules which are dry and bulky (as opposed to wet, fine, or dusty) and thus compatible with modern agricultural machinery and techniques.

The present invention enables the design of granules that release spores at a controlled rate. For instance, crops such as banana and pineapple may require spore release between 4 and 15 months after planting for optimum biocontrol.

The following examples illustrate the present invention.

EXAMPLE 1

The objectives of this experiment were 1) to form beads and granules containing viable spores of *P. penetrans,* 2) to kill nematodes contained within the beads and granules, and 3) to assess the release of viable spores from alginate beads and granules under laboratory conditions. The laboratory conditions were designed to accelerate natural degradative processes by which calcium alginate gel breaks down.

Preparation of *Pasteuria penetrans* Inoculum

Tomato plants (*Lycopersicon esculentum* cv. Ace) were infected with spore-encumbered second stage juveniles of the nematode species *Meloidogyne incognita.* The infected plants were maintained in the greenhouse for 10-12 weeks, after which they were harvested and used to prepare root inoculum by two different means as follows:

Dried root inoculum: The roots were dried at 50° C. for three days and then comminuted in a blender. The pulverized roots were then passed through a fine mesh screen of 425 microns (35 mesh).

Fresh root inoculum: Five freshly harvested roots (250 gm wet weight) were minced with water (1:2 w:v) in a blender, rinsed with 250 ml water, and passed through a 1.0 mm mesh screen (16 mesh), 50 ml of the root/water mixture was encapsulated as described below.

Encapsulation Procedures

Modifications of the procedures of Bashan, Supra (1986) and Lewis and Papavizas, Supra (1985) were used for encapsulation of the root inocula. Mixtures were prepared to yield final concentrations of 1% root inoculum (either fresh or dried), 1% sodium alginate (low or medium viscosity), and 10% kaolin in distilled water. Sodium alginate of low and medium viscosity and kaolin (a bulking agent) were purchased from Sigma Chemical Company (St. Louis, Mo.). Each mixture was stirred for one hour to produce a slurry. Beads were formed instantaneously by the dropwise addition of slurry into 150 ml of 0.1M $CaCl_2$ in a 300 ml beaker while stirring. A 10 ml serological pipet was used to deliver the drops. The beads were washed in four changes of distilled water and either kept hydrated in water or oven-dried at 50° C., for 36–48 hours. The average weight of an oven-dried granule was $9.4\pm1.3$ mg.

Attachment Assays

The attachment of *P. penetrans* spores to nematode cuticle was assessed as follows: Alginate beads or granules (containing the equivalent of 0.02 g dried, ground roots) were mixed with 28 ml distilled water and 2 ml of a suspension of 1000/ml day-old *M. incognita* juveniles. Two controls were included: a positive control consisting of 0.02 g ground root inoculum and a negative control consisting of beads prepared from ground roots without *P. penetrans.* The mixtures were bubbled with air in pharmaceutical cylinders for the indicated duration of incubation (up to 14 days for Table 1). For spore attachment assays, subsamples were transferred to Hawksley slides and the cuticles of 25 juveniles were examined for spores under the microscope at 400×. Three arbitrary classes of infection were established: (A) no spores on the cuticle; (B) 1-3 spores/juvenile, and (c), 4 or more spores/juvenile. A nematode with one or more spores on its cuticle was considered a positive reaction.

Results

In this experiment, the beads and granules were maintained in water, instead of soil, and constantly aerated to promote disintegration. The effect of oven-drying of beads was assessed as compared with hydrated (undried) beads. As explained in the legend for Table 1, the other variables in the experiment were 1) the state of the root inoculum (fresh or heat dried), and 2) the viscosity of the sodium alginate (low or medium).

Results of the in vitro attachment assay (Table 1) after 2, 5, 7 and 14 days of incubation with nematodes demonstrated that dried granules yielded a slower rate of spore release as compared with hydrated beads. Thus, after two days of incubation/aeration, the hydrated beads (W) yielded between 40% and 76% positive spore attachment. [Calculation based on sum of spore-infected nematodes, Column B plus Column C, divided by 25 (total number of nematodes samples).] In contrast, the dried granules (D) from either root preparation at Day 2 yielded only 0% to 16% positive results. By Day 14, however, the dried granules yielded 44% to 100% positive results. This suggested that dried granules could be suitable for field use since delayed release of spores is desirable. The results of this experiment also indicated that granules prepared from fresh roots were comparable to those from dried roots in release of infective spores. For instance, after seven days of incubation, fresh root preparations yielded 40% to 100% positive results, as compared with dried root preparations, which yielded 20% to 92% positive results.

TABLE 1

Release of *P. penetrans* spores from hydrated or heat-dried 1% calcium alginate beads, as influenced by the source of root sample and viscosity of sodium alginate

| State of root sample[a] | Viscosity of sodium alginate | State of alginate beads[b] | Days of Incubation: 2, Spore class[c]: A | 2: B | 2: C | 5: A | 5: B | 5: C | 7: A | 7: B | 7: C | 14: A | 14: B | 14: C |
|---|---|---|---|---|---|---|---|---|---|---|---|---|---|---|
| | | | Number of *M. incognita* juveniles with spores | | | | | | | | | | | |
| Fresh | Low | D | 23 | 2 | 0 | 14 | 11 | 0 | 9 | 13 | 3 | 0 | 12 | 13 |
| | | W | 12 | 12 | 1 | 5 | 9 | 11 | 4 | 8 | 13 | 1 | 2 | 22 |
| | Medium | D | 25 | 0 | 0 | 24 | 1 | 0 | 15 | 10 | 0 | 5 | 9 | 11 |
| | | W | 6 | 13 | 6 | 3 | 4 | 18 | 0 | 6 | 19 | 0 | 0 | 25 |
| Heat-dried | Low | D | 21 | 4 | 0 | 20 | 6 | 0 | 20 | 5 | 0 | 14 | 10 | 1 |
| | | W | 9 | 12 | 4 | 3 | 8 | 14 | 2 | 7 | 16 | 0 | 5 | 20 |
| | Medium | D | 25 | 0 | 0 | 8 | 11 | 6 | 8 | 12 | 5 | 5 | 13 | 7 |
| | | W | 15 | 10 | 0 | 9 | 15 | 1 | 6 | 13 | 6 | 1 | 11 | 13 |
| Heat-dried | NA[d] | NA[d] | 3 | 7 | 15 | 1 | 2 | 22 | 0 | 0 | 25 | 0 | 2 | 23 |

[a]Root samples containing *P. penetrans* were either heat-dried at 50° C., ground to pass a 425 um mesh sieve before use or blended fresh and screened through a 1000 um mesh sieve before use for alginate bead preparation.
[b]Alginate beads were either dried at 50° C. before attachment assays (D) or used in the hydrated state (W).
[c]Spore attachment classes were as follows: A, no spores; B, 1-3 spores/juvenile, and C, 4 or more spores/juvenile.
[d]Not applicable, a positive control consisting of 425 um sample.

EXAMPLE 2

This in planta experiment was designed to evaluate the slow-release of spores from spore-laden granules and spore attachment to nematodes as they parasitized greenhouse-grown tomato plants. Two kg pots were set up with overhead misting twice a day to simulate rainfall.

The experiment was designed with six different treatments, eight replicates for each treatment, in a split-pot set-up, with time of harvest (4, 8, 12, 16, 20 weeks) as the main plots and granular treatments as the sub-plots. Pots containing two-week-old seedlings previously infected with 1000 juveniles/plant of *M. incognita* received either 1.0 g/pot of granules or 0.1 g of ground root inoculum. The granules were prepared as described in Example 1 from fresh or dried root inoculum, and subsequently oven-dried at 50 C. Prior to use in this experiment, all granules were assayed as described in Example 1 and found to perform in vitro comparably to those in Example 1.

At each harvest, the root systems were washed, dried for 48 hours at 50° C., ground to pass a 35 mesh screen (425 microns), and analyzed for *P. penetrans* spore attachment in the in vitro assay described in Example 1. For each of the eight replicates, 25 nematodes were examined for spore attachment. The results were averaged for each treatment and listed in Table 2 as the mean number of nematodes with spores per sample of 25 namatodes. [Values between 0 and 1 indicate that one or more of the eight replicate samples contained no infected namatodes. Fractional values are the result of averaging the eight replicate values.]

TABLE 2

Slow-release of *P. penetrans* spores from calcium alginate granules applied to the rhizospheres of *M. incognita*-infested tomatoes over 20 weeks under greenhouse conditions.

| Treatment: Incolum[a] | g/pot | 4 weeks, Number of spores/juvenile: 0 | 4 weeks: 1-3 | 4 weeks: 4 | 8 weeks: 0 | 8 weeks: 1-3 | 8 weeks: 4 | 12 weeks: 0 | 12 weeks: 1-3 | 12 weeks: 4 | 16 weeks: 0 | 16 weeks: 1-3 | 16 weeks: 4 | 20 weeks: 0 | 20 weeks: 1-3 | 20 weeks: 4 |
|---|---|---|---|---|---|---|---|---|---|---|---|---|---|---|---|---|
| | | Mean Number of *M. incognita* juveniles with spores | | | | | | | | | | | | | | |
| Fresh LV | 1.0 | 25 | 0 | 0 | 25 | 0 | 0 | 25 | 0 | 0 | 24.9 | 0.1 | 0 | 24.6 | 0.4 | 0 |
| Fresh MV | 1.0 | 25 | 0 | 0 | 25 | 0 | 0 | 25 | 0 | 0 | 24.8 | 0.2 | 0 | 24.4 | 0.6 | 0 |
| Dry LV | 1.0 | 25 | 0 | 0 | 25 | 0 | 0 | 25 | 0 | 0 | 21.4 | 3.6 | 0 | 1.8 | 4.1 | 2.1 |
| Dry MV | 1.0 | 25 | 0 | 0 | 25 | 0 | 0 | 25 | 0 | 0 | 23.1 | 1.9 | 0 | 20.2 | 4.6 | 0.1 |
| Dry Inoc[b] | 0.1 | 24.9 | 0.1 | 0 | 25 | 0 | 0 | 23.7 | 1.1 | 0.2 | 6.1 | 8.5 | 10.4 | 0.9 | 3.9 | 20.2 |
| Noninoc MV | 1.0 | 25 | 0 | 0 | 25 | 0 | 0 | 25 | 0 | 0 | 25 | 0 | 0 | 25 | 0 | 0 |

[a]Granules were prepared with fresh root inoculum and low (LV) or medium (MV) viscosity alginate and with dried root preparation with low or medium viscosity alginate. Dried root preparation (DryInoc) was applied directly to rhizospheres, Noninoc MV refers to granules prepared from non-infected, dried roots and MV alginate.
[b]Each assay routinely included a positive control for the assay consisting of 0.02 g of dry inoculum. The average number of nematodes with positive-control spores were: 0, 3.0 and 22.0 at 4 weeks; 3.5, 8.5 and 13.0 at 8 weeks; 2.0, 11.0 and 12.0 after 12 weeks; 7.0, 11.5 and 6.5 at 16 weeks; and 3.0, 8.5 and 13.5 at 20 weeks.

The percentage of positive results for the unencapsulated powdered inoculum (positive control) was 5.2, 75.6, and 96.4 after 12, 16 and 20 weeks respectively.

The granular treatments were superior to the powdered inoculum in that release was delayed until after 12 weeks in soil. After 16 weeks, granules prepared from dried inoculum yielded 7.6% to 14.4% positive results, and after 20 weeks, the results were 18.8% to 24.8% positive. Granules prepared from fresh inoculum yielded 0.4% to 0.8% positive results after 16 weeks and 1.6% to 2.4% positive results after 20 weeks.

In this in planta experiment, granules prepared from fresh inoculum were less infective than granules prepared from dried inoculum. However, the level of infectivity of fresh-inoculum granules were considered to be sufficient for practical use on certain crops, such as banana and pineapple.

In summary, the results indicated that dried granules, from either fresh or dried inoculum, performed adequately in planta to release active spores of *P. penetrans.*

What is claimed is:

1. Biocontrol particles for treating plants infested with nematodes, said biocontrol particles comprising biodegradable granules containing comminuted root inoculum containing viable *Pasteuria penetrans* spores grown in nematode hosts, said granules being dried to a moisture content below about 15%, said root inoculum being subjected to a heat treatment combination of temperature and duration that is lethal for at least a portion of said nematode hosts, wherein said heat treatment is at a temperature between about 48° C. and 52° C. for a duration of about 12 to 48 hours.

2. The biocontrol particles of claim 1 in which said heat treatment occurs during drying of the granules.

3. The biocontrol particles of claim 2 further comprising the step wherein said root inoculum is dried prior to granule formation at ambient room temperature.

4. The biocontrol particles of claim 3 wherein said ambient temperature is between about 15° to 40° C.

5. The biocontrol particles of claim 1 further comprising the step wherein said root inoculum is dried prior to granule formation.

6. The biocontrol particles of claim 1 in which said heat treatment occurs prior to granule formation, and further comprising the step of drying of the granules at ambient temperatures of between about 15° to 40° C.

7. The biocontrol particles of claim 1 in which said biodegradable granules comprise calcium alginate formed in situ around said comminuted roots.

8. A method for killing or inhibiting the reproduction of namatodes in plants infected with nematodes comprising the steps of depositing near said plants an effective amount of biodegradable granules containing comminuted root inoculum containing viable *Pasteuria penetrans* spores grown in nematode hosts, said granules being dried to a moisture content below about 15%, said root inoculum being subjected to a heat treatment combination of temperature and duration that is lethal for at least a portion of said nematode hosts, wherein said heat treatment is at a temperature between about 48° C. and 52° C. for a duration of about 12 to 48 hours.

9. A method for the preparation of biocontrol particles suitable for depositing near plants infected with nematodes for the purpose of killing or inhibiting the reproduction of the nematodes, said method comprising the steps of encapsulating comminuted root inoculum containing viable *Pasteuria penetrans* spores grown in nematode hosts in biodegradable granules capable of controlled release of the *Pasteuria penetrans* spores, and drying said granules to a moisture content below about 15%, wherein said root inoculum is subjected to a heat treatment combination of temperature and duration that is lethal for at least a portion of said nematode hosts, and wherein said heat treatment is at a temperature between about 48° C. and 52° C. for a duration of about 12 to 48 hours.

* * * * *